US007344877B1

(12) United States Patent
Camacho et al.

(10) Patent No.: US 7,344,877 B1
(45) Date of Patent: Mar. 18, 2008

(54) BIOMOLECULE MICROARRAY SUPPORT

(76) Inventors: Joseph Camacho, 1662 8th Ave., San Francisco, CA (US) 94122; Greg Richardson, 2051 Menalto Ave., Menlo Park, CA (US) 94025

( * ) Notice: Subject to any disclaimer, the term of this patent is extended or adjusted under 35 U.S.C. 154(b) by 454 days.

(21) Appl. No.: 11/026,764

(22) Filed: Dec. 31, 2004

(51) Int. Cl.
*C12M 3/00* (2006.01)

(52) U.S. Cl. .................................................. 435/287.2

(58) Field of Classification Search ............. 435/287.2, 435/287.8, 287.9, 288.4, 288.5, 288.6; 422/50, 422/56, 57–60
See application file for complete search history.

(56) References Cited

U.S. PATENT DOCUMENTS 4,450,231 A * 5/1984 Ozkan ....................... 435/7.92
6,168,914 B1 * 1/2001 Campbell et al. .............. 435/4
6,464,942 B2 * 10/2002 Coffman et al. ............ 422/100

* cited by examiner

*Primary Examiner*—Ann Y. Lam
(74) *Attorney, Agent, or Firm*—Jack Lo

(57) ABSTRACT

A biomolecule microarray support is comprised of a frame with upward projecting side walls. A transparent substrate is detachably positioned on the frame within the walls. A printed hydrophobic grid is arranged on the substrate for receiving spots of biomolecule samples. Each square on the grid is identified with a position number. A resilient gasket with an array of chambers is position on the substrate in alignment with the grid. The chambers are defined by dividing walls which are tapered from top to bottom. A clamping plate is positioned on the gasket which is received in stabilizing grooves under the clamping plate. Holes on the clamping plate aligned with the chambers allow a hybridization fluid to be introduced into the chambers. Fasteners connect the clamping plate and the frame to tightly compress the gasket against the substrate to seal the chambers from each other.

1 Claim, 3 Drawing Sheets

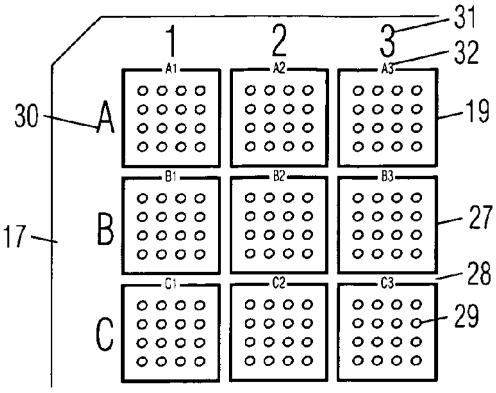
Fig. 2
Fig. 3
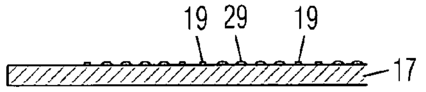
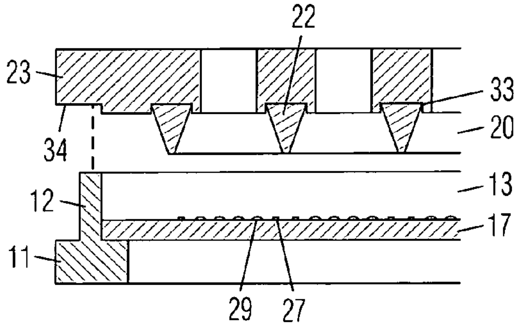
Fig. 4
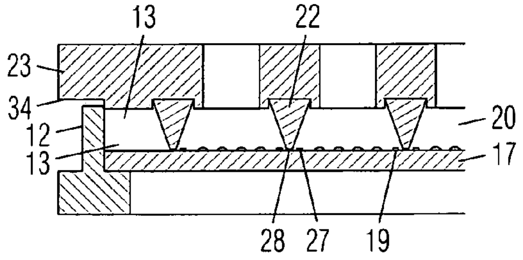
Fig. 5
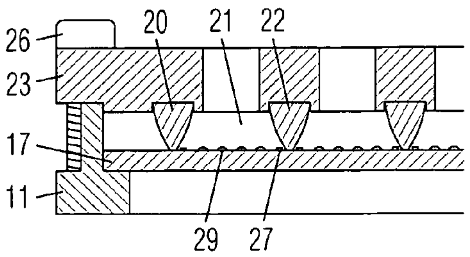
Fig. 6

BIOMOLECULE MICROARRAY SUPPORT

BACKGROUND OF THE INVENTION

1. Field of the Invention

The invention broadly relates to devices for supporting biomolecule samples for laboratory analysis.

2. Prior Art

Analysis of biomolecule samples is typically performed by depositing small spots of different molecules in a microarray on a supporting device. The spots are dried, and a solution containing an unknown with chemical tags is applied to the dried droplets. Binding reactions or hybridization occur where the unknown binds to the spots. The tags in the complementary compounds in the solution are detected by optical or radiosensitive scanning.

A typical supporting device is comprised of a glass plate and a divider thereon which defines an array of chambers for receiving the spots and solution. Some prior art devices have dividers permanently attached to the glass plates with adhesive. Such fixed dividers interfere with spot deposition and scanning. Further, the adhesive requires a relatively wide contact area at the bottom of the divider provided by divider side walls which are perpendicular to the glass plate. However, the thick side walls reduce the usable chamber areas. Some supporting devices have dividers with thick side walls but instead of using adhesive, clamp the dividers upon the glass plates. The thick side walls are compressed relatively lightly against the glass plates so leakage between chambers may occur.

BRIEF SUMMARY OF THE INVENTION

A biomolecule microarray support is comprised of a frame with upward projecting side walls. A transparent substrate is detachably positioned on the frame within the walls. A printed hydrophobic grid is arranged on the substrate for receiving spots of biomolecule samples. Each square on the grid is identified with a position number. A resilient gasket with an array of chambers is position on the substrate in alignment with the grid. The chambers are defined by dividing walls which are tapered from top to bottom. A clamping plate is positioned on the gasket which is received in stabilizing grooves under the clamping plate. Holes on the clamping plate aligned with the chambers allow a hybridization fluid to be introduced into the chambers. Fasteners connect the clamping plate and the frame to tightly compress the gasket against the substrate to seal the chambers from each other.

BRIEF DESCRIPTION OF THE SEVERAL VIEWS OF THE DRAWING

FIG. 2 shows a grid on a transparent substrate thereof.

FIG. 3 is a sectional view of the substrate with spots of biomolecule samples.

FIG. 4 is a sectional view of the biomolecule microarray support during assembly.

FIG. 5 shows the biomolecule microarray support partially assembled but before the gasket is compressed.

FIG. 6 shows the biomolecule microarray support fully assembled and the gasket compressed.

DRAWING REFERENCE NUMERALS

| | |
|---|---|
| 10. Support | 11. Frame |
| 12. Wall | 13. Wall |
| 14. Opening | 15. Shoulder |
| 16. Fastener Hole | 17. Substrate |
| 18. Organic Coating | 19. Hydrophobic Grid |
| 20. Gasket | 21. Chamber |
| 22. Dividing Wall | 23. Clamping Plate |
| 24. Hole | 25. Fastener Hole |
| 26. Fastener | 27. Square |
| 28. Gap | 29. Biomolecule Sample |
| 30. Row Identifying Indicia | 31. Column Identifying Indicia |
| 32. Square Identifying Indicia | 33. Recessed Grid |
| 34. Peripheral Shoulder | 35. Hybridization Fluid |

DETAILED DESCRIPTION OF THE INVENTION

FIG. 1

Figure 1:
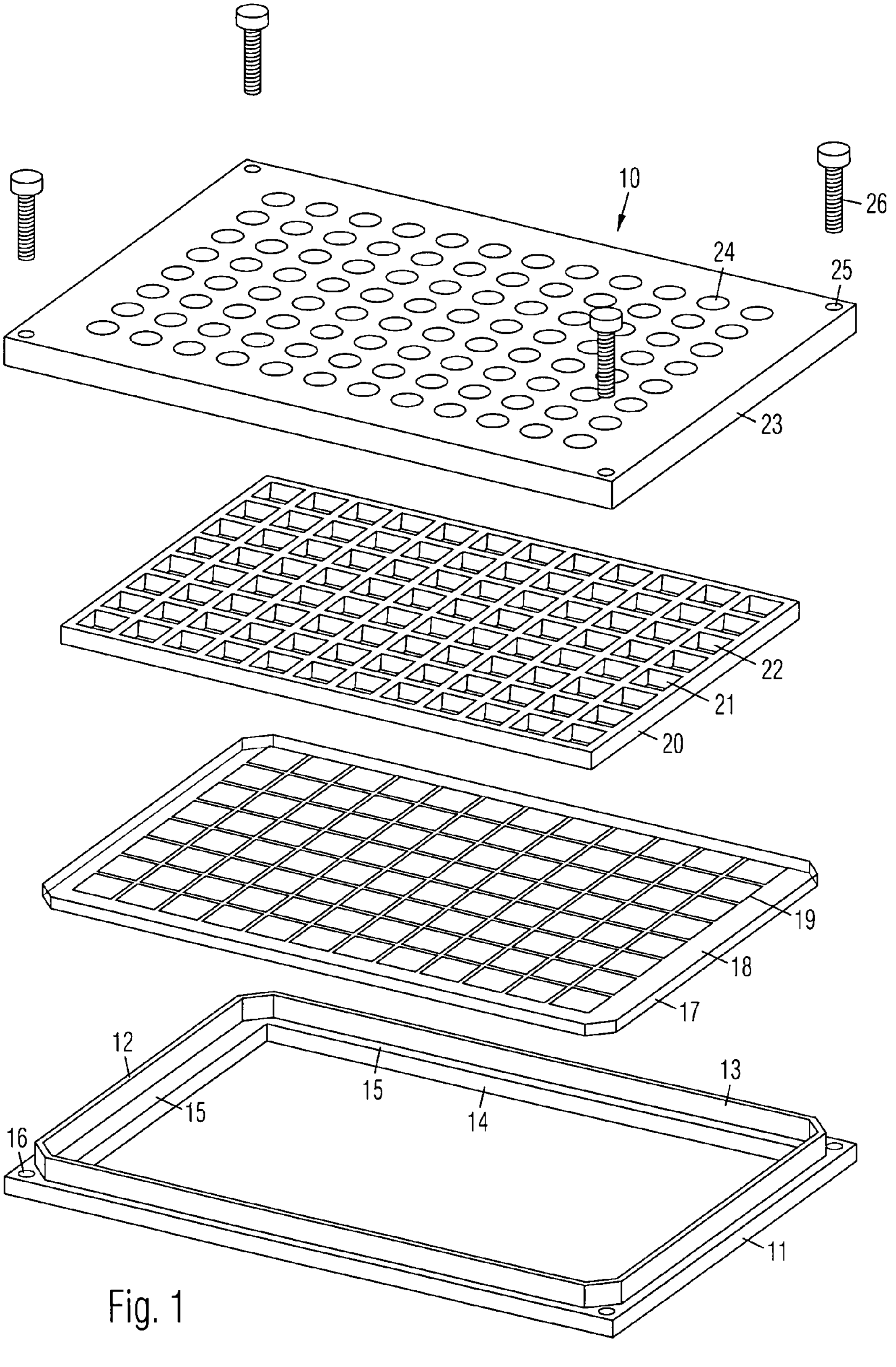
FIG. 1 is an exploded view of a biomolecule microarray support.

A preferred embodiment of a biomolecule microarray support 10 is shown in an exploded view in FIG. 1. It is comprised of a frame 11 with upward projecting side walls 12 and 13 surrounding an opening 14. Side walls 12 and 13 may be connected as shown or they may be discontinuous. There is a shoulder 15 around opening 14. First fastener holes 16 are positioned at respective corners of frame 11.

A transparent plate or substrate 17 is for detachably positioning on frame 11 within side walls 12 and 13 in alignment with opening 14 and supported by shoulder 15. There is an organic coating 18 on top of substrate 17 to help bind biomolecules. A printed hydrophobic grid 19 is arranged on substrate 17 for separating spots of biomolecule samples. A resilient grid-shaped gasket 20 with an array of chambers 21 is for positioning on substrate 17 in alignment with grid 19. Chambers 21 are defined by intersecting dividing walls 22.

A clamping plate 23 is for positioning on gasket 20. Holes 24 on clamping plate 23 are aligned with chambers 21 for allowing introduction of a hybridization fluid into chambers 21. Second fastener holes 25 are positioned at respective corners of clamping plate 23. Fasteners 26 are for positioning through first and second fastener holes 16 and 25 to connect frame 11 and clamping plate 23 to tightly compress gasket 20 against substrate 17 to seal chambers 21 from each other.

FIG. 2

An upper left corner of substrate 17 is shown in a top view in FIG. 2. Grid 19 is comprised of individual squares 27 of hydrophobic ink separated from each other by gaps 28. A microarray of spots of biomolecule samples 29 have been deposited on substrate 17 within each square 27. The number of spots in each square may vary, but the larger the square, the more spots may be deposited.

In this example, grid 19 includes twelve columns and eight rows for a total of ninety-six squares. Row identifying indicia 30 and column identifying indicia 31 are arranged along orthogonal edges of substrate 17. In this example, row identifying indicia 30 are comprised of letters and column identifying indicia 31 are comprised of numbers. Individual square identifying indicia 32 are arranged adjacent each square 27, and are each comprised of a combination of the respective row and column identifying indicia, for example, A1 and A2 for the first two squares on the first row, B1 and B2 for the first two squares on the second row, etc. The identifying indicia may be machine read by a laser scanner or fluorescence reader for more automation.

FIG. 3

In FIG. 3, substrate 17 is preferably detached from the frame when biomolecule samples 29 are deposited on grid 19 to avoid having the frame interfere with robotic deposition equipment.

FIG. 4

In FIG. 4, substrate 17 is positioned on frame 11 within walls 12 and 13. Gasket 20 is secured in a recessed grid 33 on a bottom of clamping plate 23, preferably by spring clips. Recessed grid 33 is shaped to match grid-shaped gasket 20 to stabilize dividing walls 22 between hydrophobic squares 27. Dividing walls 22 of gasket 20 are sharply tapered from a wide top to a narrow bottom. A peripheral shoulder 34 on the bottom of clamping plate 23 is aligned with walls 12 and 13.

FIG. 5

In FIG. 5, gasket 20 is loosely positioned on substrate 17. Peripheral shoulder 34 is mated with the top of walls 12 and 13 to align gasket 20 with grid 19. The narrow bottoms of dividing walls 22 are positioned in gaps 28 between squares 27 of grid 19.

FIG. 6

In FIG. 6, clamping plate 23 is secured to frame 11 with fasteners 26. Gasket 20 is compressed tightly between clamping plate 23 and substrate 17, as indicated by the bowing of dividing walls 22. The clamping force is concentrated on the narrow bottoms of tapered dividing walls 22 to positively seal chambers 21 from each other. The narrow bottoms of tapered dividing walls 22 allow larger chambers 21, which allow larger squares 27, which allow more spots of biomolecules 29.

FIG. 7

Figure 7:
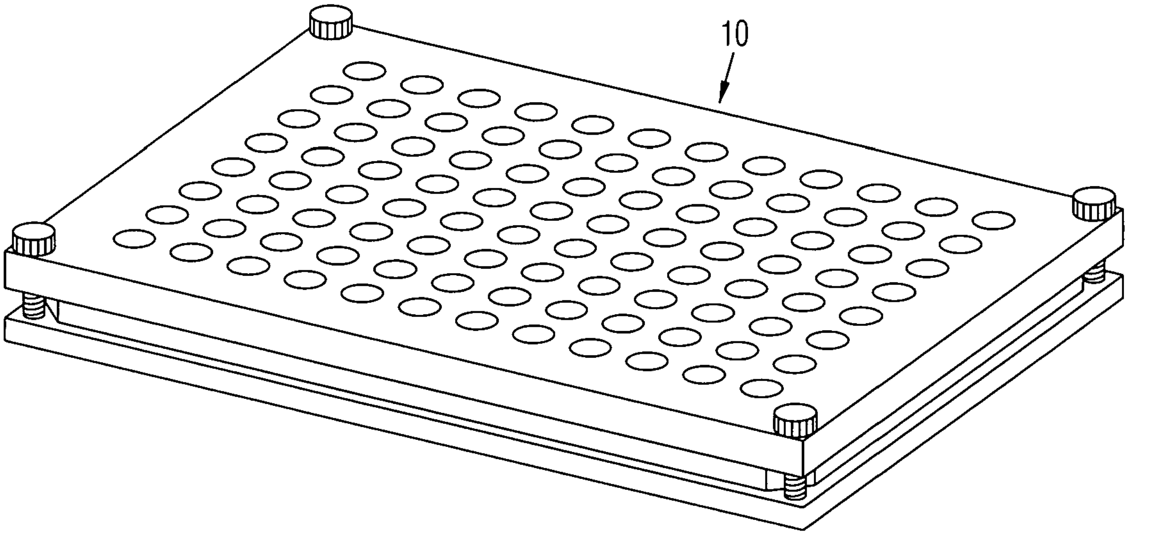
FIG. 7 is a perspective view of the assembled biomolecule microarray support.
Figure 8:
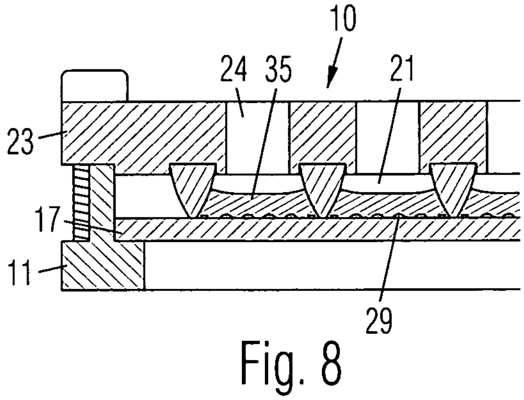
FIG. 8 shows the chambers in the biomolecule microarray support filled with a hybridization fluid.

The biomolecule microarray support 10 is shown in FIG. 7 full assembled.

FIG. 8

A hybridization fluid 35 is introduced into chambers 21 through holes 24 in clamping plate 23 to react with biomolecule samples 29. After hybridization, clamping plate 23 is detached from frame 11, and substrate 17 may be removed from frame 11 for scanning without interference from frame 11 for reduced background, reduced light scattering, and better resolution.

Although the foregoing description is specific, it should not be considered as a limitation on the scope of the invention, but only as an example of the preferred embodiment. Many variations are possible within the teachings of the invention. For example, different attachment methods, fasteners, materials, dimensions, etc. can be used unless specifically indicated otherwise. The relative positions of the elements can vary, and the shapes of the elements can vary. Therefore, the scope of the invention should be determined by the appended claims and their legal equivalents, not by the examples given.

We claim:

1. A biomolecule microarray support, comprising:

a frame;

a substrate detachably positioned on top of the frame;

a hydrophobic grid on the substrate for separating spots of biomolecule samples deposited on the substrate;

a resilient grid-shaped gasket with an array of chambers defined by intersecting dividing walls detachably positioned on the substrate in alignment with the hydrophobic grid, wherein the dividing walls of the gasket are tapered from top to bottom for concentrating pressure at the narrower bottom for better sealing;

a clamping plate detachably positioned on top of the gasket, wherein holes on the clamping plate are aligned with the chambers in the gasket for allowing introduction of a fluid into the chambers; and fasteners detachably connecting the clamping plate to the frame and compressing the gasket there between.

* * * * *